(12) United States Patent
Lee

(10) Patent No.: US 9,706,989 B2
(45) Date of Patent: Jul. 18, 2017

(54) MEDICAL SUTURE PACKAGE

(71) Applicant: SM Eng. Co., Ltd., Busan (KR)

(72) Inventor: Gil Soo Lee, Busan (KR)

(73) Assignee: SM Eng. Co., Ltd., Busan (KR)

( * ) Notice: Subject to any disclaimer, the term of this patent is extended or adjusted under 35 U.S.C. 154(b) by 101 days.

(21) Appl. No.: 14/734,436

(22) Filed: Jun. 9, 2015

(65) Prior Publication Data

US 2015/0366559 A1 Dec. 24, 2015

(30) Foreign Application Priority Data

Jun. 19, 2014 (KR) ........................ 10-2014-0074716

(51) Int. Cl.
*A61B 17/06* (2006.01)
*A61B 17/00* (2006.01)

(52) U.S. Cl.
CPC ...... *A61B 17/06133* (2013.01); *A61B 2017/0084* (2013.01); *A61B 2017/06142* (2013.01)

(58) Field of Classification Search
CPC ...... A61B 17/06133; A61B 2017/0084; A61B 2017/06142; A61B 17/06166; A61B 17/04; A61B 17/06144; A61B 19/02
USPC .............................................. 206/63.3, 210
See application file for complete search history.

(56) References Cited

U.S. PATENT DOCUMENTS

| | | | | |
|---|---|---|---|---|
| 4,961,498 A * | 10/1990 | Kalinski | .......... | A61B 17/06133 206/339 |
| 5,236,083 A * | 8/1993 | Sobel | ............... | A61B 17/06133 206/227 |
| 5,271,495 A * | 12/1993 | Alpern | ............. | A61B 17/06133 206/380 |
| 5,887,706 A * | 3/1999 | Pohle | ............... | A61B 17/06133 206/227 |
| 6,047,815 A * | 4/2000 | Cerwin | ........... | A61B 17/06133 206/225 |
| 8,960,422 B2 * | 2/2015 | Reyhan | ............ | A61B 17/06114 206/210 |
| 2003/0010655 A1 * | 1/2003 | Alpern | ............. | A61B 17/06133 206/63.3 |
| 2006/0226031 A1 * | 10/2006 | Kennedy | ......... | A61B 17/06133 206/63.3 |

(Continued)

FOREIGN PATENT DOCUMENTS

EP 1475046 A1 11/2004
JP 11206775 A 8/1999

(Continued)

*Primary Examiner* — Chun Cheung
(74) *Attorney, Agent, or Firm* — Novick, Kim & Lee, PLLC; Jae Youn Kim

(57) ABSTRACT

Provided herein is a medical suture package that enables a medical suture to be wound therearound, stored therein, and carried, and which allows the suture to be drawn out when needed. The medical suture package is configured such that, when the suture is drawn out, friction between the suture and a main body of the package can be reduced, thus preventing a curling phenomenon, and making the operation of drawing out the suture easy. Particularly, even if external force is applied to the main body, a winding depression that is formed in the main body and in which the suture is wound around the main body can be maintained in shape, thus ensuring ease of the drawing-out of the suture, thereby markedly enhancing convenience in use.

9 Claims, 10 Drawing Sheets

(56) References Cited

U.S. PATENT DOCUMENTS

| | | | | |
|---|---|---|---|---|
| 2007/0227914 A1* | 10/2007 | Cerwin | ............ | A61B 17/06133 206/63.3 |
| 2010/0044270 A1* | 2/2010 | Noble | .................... | B65D 83/04 206/538 |
| 2010/0163435 A1* | 7/2010 | Fischer | ............ | A61B 17/06114 206/204 |
| 2012/0055828 A1* | 3/2012 | Kennedy | .......... | A61B 17/06133 206/363 |

FOREIGN PATENT DOCUMENTS

| KR | 10-2012-0004489 A | 1/2012 |
|---|---|---|
| KR | 10-2013-0018751 A | 2/2013 |

\* cited by examiner

MEDICAL SUTURE PACKAGE

BACKGROUND OF THE INVENTION

1. Field of the Invention

The present invention generally relates to medical suture packages that enable medical sutures to be wound therearound, stored therein, and carried, and which allow the sutures to be drawn out of the packages when needed. More particularly, the present invention relates to a medical suture package that is configured such that, when a suture is drawn out, friction between the suture and a main body of the package can be reduced, thus preventing a curling phenomenon, and making the operation of drawing out the suture easy, and such that even if external force is applied to the main body, a winding depression that is formed in the main body and in which the suture is wound around the main body can be maintained in its original shape, thus ensuring ease of the drawing-out of the suture, thereby markedly enhancing convenience in use.

2. Description of the Related Art

Generally, medical sutures are used to hold body tissues together to close a surgical opening of the body of a patient after an injury or surgery. Such a suture is stored in an aseptic package, is opened in a place for an operation, and is drawn out of the package before being used to hold body tissues. A suture needle is typically provided on one end of such a suture, thus forming a medical device set.

Suture packages are devices for storing and carrying sutures in aseptic conditions and allowing the sutures to be drawn out when needed. There have been many advances in the field of such suture packages. Representative examples were proposed in Korean Patent Unexamined Publication No. 10-2012-0004489, entitled "Packaged Antimicrobial Medical Device and Method of Manufacturing the Same", and Korean Patent Unexamined Publication No. 10-2013-0018751, entitled "Suture Package Providing Unconstrained Dispensing of Suture and Method therefor".

Referring to the former gazette, the medical device includes a base having a storage space therein, and a cover that is provided on a peripheral edge of the base so as to cover the storage space. The base has an elliptical shape. The suture is wound around the base such that the suture is disposed in the storage space, and then the end of a suture needle is held by a fixing clip. Thereafter, the medical device is packaged. In this state, when drawing out the suture from the medical device, a medical worker uses pincers, holds the needle, and pulls it in a diagonal direction. When pulling the needle out of the medical device, the suture that has been wound in the storage space strongly rubs an inner sidewall of the storage space, so that the suture may not be easily drawn out. In this case, the medical worker generally more strongly pulls the suture out of the device. However, because the suture is drawn out in a diagonal direction, the suture may be moved toward the cover and a fixing protrusion provided for fixing the cover to the base and thus caught between the cover and the fixing protrusion. In this case, the suture cannot be easily drawn out, and even if it has been drawn out, it may become impossible to use it because of a curling phenomenon.

Referring to the latter gazette, the suture package includes a first part and a second part, configured such that a suture is wound in the package and then the first and second parts are closed to each other to store the suture. However in the same manner as the former, when a medical worker holds a suture needle and draws it out of the package, the suture may be caught in space formed between the first and second parts and thus not easily drawn out.

In an effort to overcome the above-mentioned problems, a medical suture package having an improved structure was introduced in Korean Patent Registration No. 10-1488777. In this technique, a winding depression is formed in a peripheral surface of a main body. Protrusion rods are provided on a curved portion of a sidewall of the winding depression so as to reduce friction a suture and the main body when the suture is drawn out of the main body. However, when a medical worker grasps the main body to draw out the suture from the package, the width of the winding depression may be reduced by external force applied to the upper and lower surfaces of the main body, thus impeding the operation of drawing out the suture.

SUMMARY OF THE INVENTION

Accordingly, the present invention has been made keeping in mind the above problems occurring in the prior art, and an object of the present invention is to provide a medical suture package that has an improved structure such that when a suture is drawn out of the package, the friction between the suture and the package can be reduced, thus preventing a curling phenomenon and making it easy to draw out the suture, and which is particularly configured such that, even if external force is applied to the main body, the winding depression in which the suture is wound around the main body can be maintained in its original shape, thus ensuring the operation of drawing out the suture, thereby markedly enhancing convenience in use.

In order to accomplish the above object, in an aspect, the present invention provides a medical suture package, including: a main body including upper and lower body parts respectively provided at upper and lower positions along a perimeter of the main body, with a winding depression formed between the upper and lower body parts such that the winding depression is open outward so that a suture is wound around the main body in the winding depression; a fixing clip provided at a predetermined position on an upper surface of the main body so that a suture needle provided on a first end of the suture wound the main body in the winding depression is fitted into and held by the fixing clip; and a protrusion rod provided on a curved surface of an inner sidewall of the winding depression formed in the main body, the protrusion rod supporting the suture so that the suture wound the main body is prevented from making direct contact with at least the curved surface of the inner sidewall of the winding depression.

A communication slot may be formed at a predetermined position in the upper body part so that the winding depression communicates with the fixing clip through the communication slot.

A plurality of insert holes may be formed in at least either of the upper and lower body parts so that a second end of the suture can be fitted into any one of the insert holes.

In another aspect, the present invention provides a medical suture package, including: a main body including upper and lower body parts respectively provided at upper and lower positions along a perimeter of the main body, with a winding depression formed between the upper and lower body parts such that the winding depression is open outward so that a suture is wound around the main body in the winding depression, and with a plurality of coupling holes formed in a perimeter of the upper body part; a fixing clip provided at a predetermined position on an upper surface of the main body so that a suture needle provided on a first end of the suture wound the main body in the winding depression is fitted into and held by the fixing clip; a protrusion rod provided on a curved surface of an inner sidewall of the winding depression formed in the main body, the protrusion rod supporting the suture so that the suture wound the main body is prevented from making direct contact with at least the curved surface of the inner sidewall of the winding depression; and a plurality of supports disposed between the upper and lower body parts of the main body, the supports supporting the upper and lower body parts so that even when an external force is applied to the main body, the upper and lower body parts are prevented from making contact with each other and the winding depression is thus maintained in shape, with an insert part provided on a first end of each of the supports, the insert part being fitted into the corresponding coupling hole of the upper body part.

A second end of each of the support may be coupled to the lower body part so that, when the support is bent upward on the second end thereof, the support is disposed between the upper and lower body parts and coupled to the upper body part by the insert part fitted into the corresponding coupling hole.

A communication slot may be formed at a predetermined position in the upper body part so that the winding depression communicates with the fixing clip through the communication slot.

A plurality of insert holes may be formed in at least either of the upper and lower body parts so that a second end of the suture can be fitted into any one of the insert holes.

In a further aspect, the present invention provides a medical suture package, including: a main body including upper and lower body parts respectively provided at upper and lower positions along a perimeter of the main body, with a winding depression formed between the upper and lower body parts such that the winding depression is open outward so that a suture is wound around the main body in the winding depression, wherein an inner sidewall of the winding depression includes a saw-toothed part provided for reducing a contact surface area between the suture and the main body and minimizing friction therebetween, the saw-toothed part including protrusions and recesses that alternate each other; and a fixing clip provided at a predetermined position on an upper surface of the main body so that a suture needle provided on a first end of the suture wound the main body in the winding depression is fitted into and held by the fixing clip.

BRIEF DESCRIPTION OF THE DRAWINGS

The above and other objects, features and advantages of the present invention will be more clearly understood from the following detailed description taken in conjunction with the accompanying drawings, in which.

DESCRIPTION OF THE PREFERRED EMBODIMENTS

Hereinafter, exemplary embodiments of a medical suture package according to the present invention will be described in detail with reference to the attached drawings.

The terms and words used in the specification and claims must not be limited to typical or dictionary meanings, but must be regarded as concepts selected by the inventor as concepts best illustrating the present invention, and must be interpreted as having meanings and concepts adapted to the scope and spirit of the present invention to aid in understanding the technology of the present invention.

Therefore, the construction of the embodiment illustrated in the specification and the drawings must be regarded as only one illustrative example, and these are not intended to limit the present invention. Furthermore, it must be understood that various modifications, additions and substitutions are possible at the point of time of application of the present invention.

Figure 1:
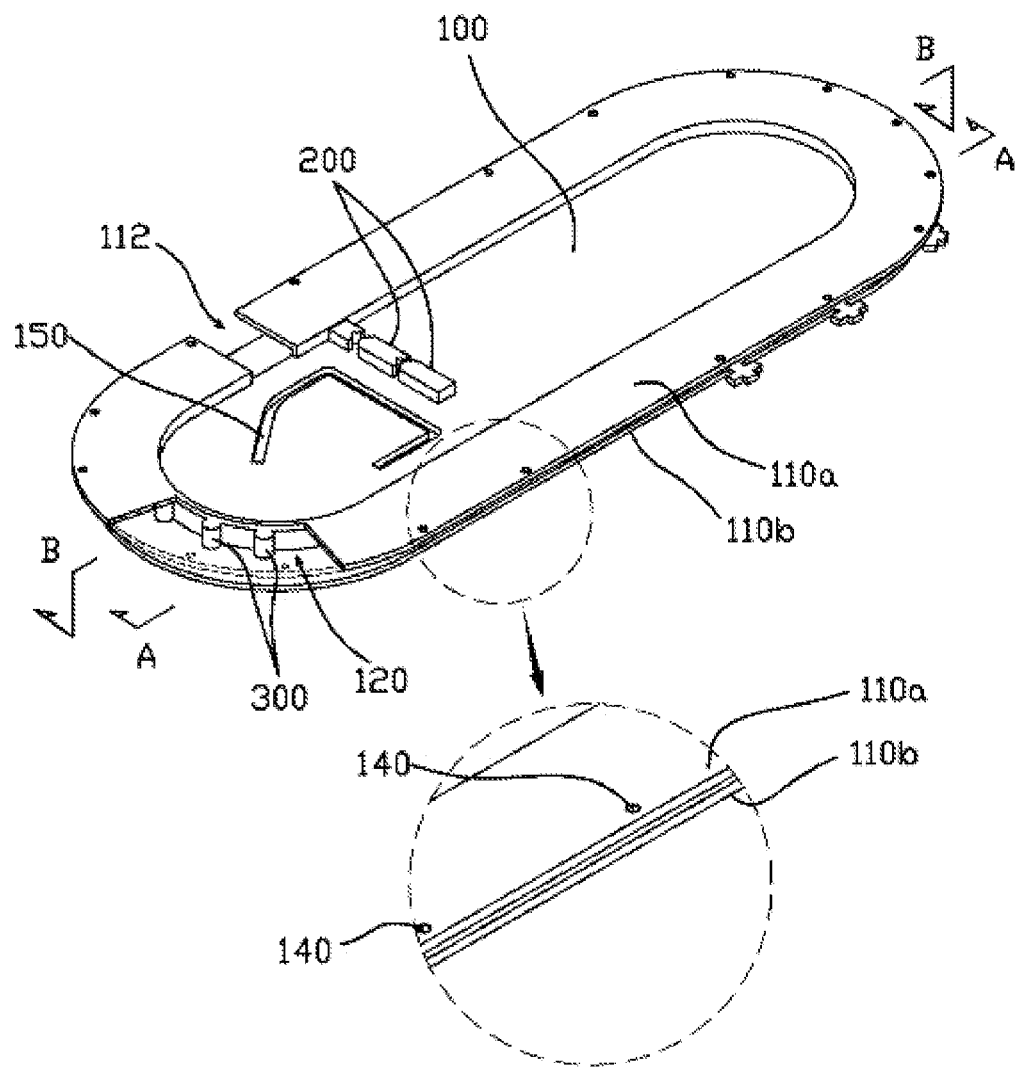
FIG. 1 is a partially-exploded perspective view illustrating a medical suture package according to a first embodiment of the present invention.
Figure 2:
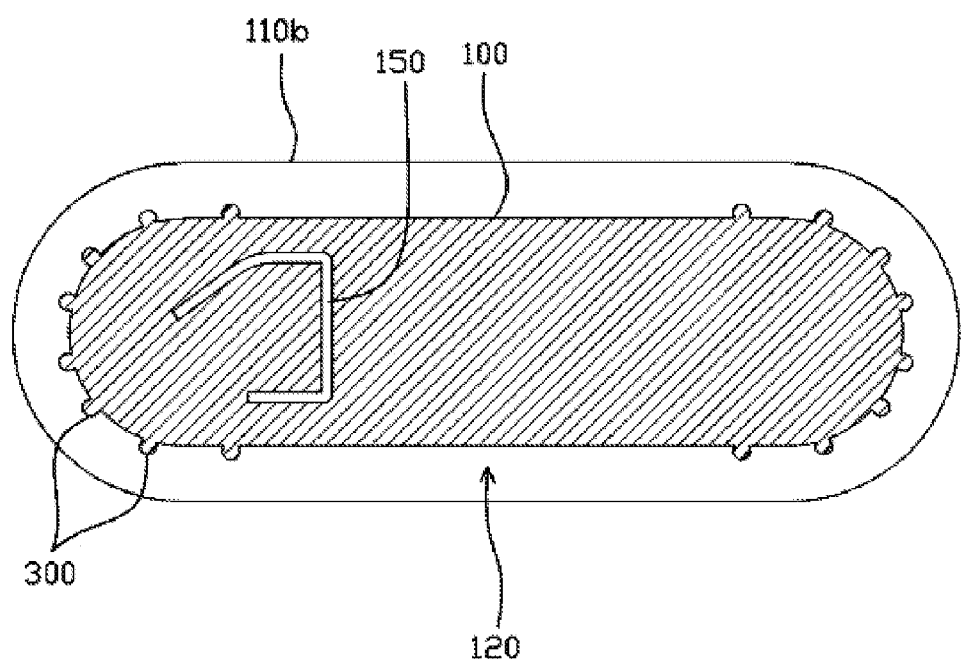
FIG. 2 is a sectional view taken along line A-A of FIG. 1.
Figure 3:
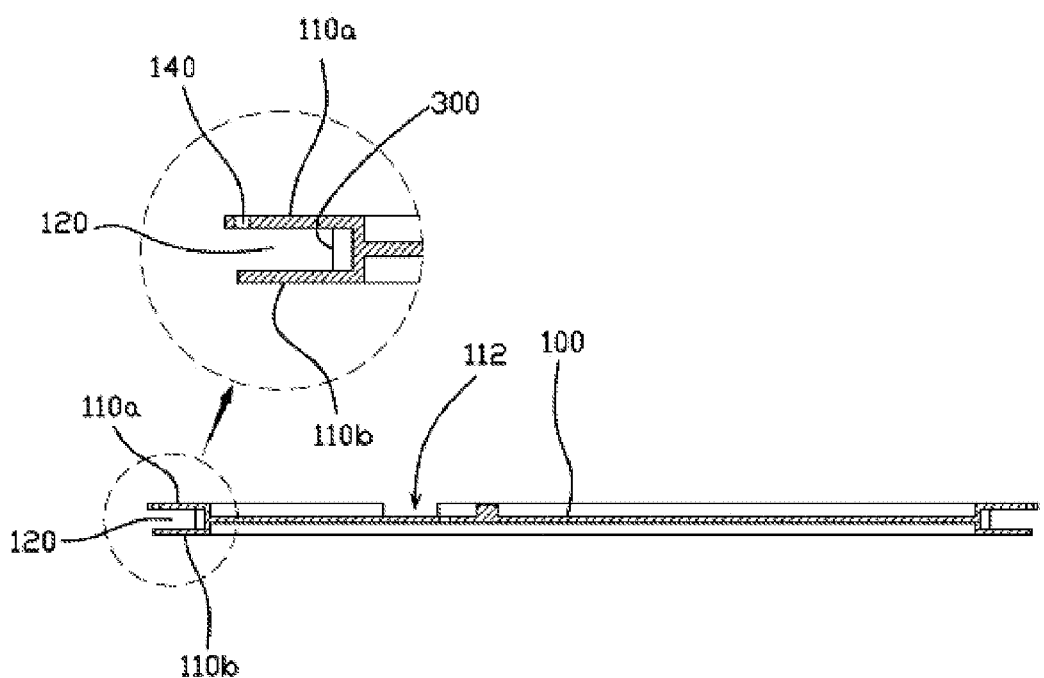
FIG. 3 is a sectional view taken along line B-B of FIG. 1.

FIG. 1 is a partially-exploded perspective view illustrating a medical suture package according to a first embodiment of the present invention. FIG. 2 is a sectional view taken along line A-A of FIG. 1. FIG. 3 is a sectional view taken along line B-B of FIG. 1.

Referring to FIGS. 1 through 3, the medical suture package according to the first embodiment of the present invention includes a main body 100, a fixing clip 200, and protrusion rods 300.

The main body 100 has an elliptical shape and includes upper and lower body parts 110a and 110b that are respectively provided at upper and lower positions along the perimeter of the main body 100, with a winding depression 120 formed between the upper and lower body parts 110a and 110b such that it is open outward. A communication slot 112 is formed at a predetermined position in the upper body part 110a so that the winding depression 120 communicates with an upper surface of the main body 100 through the communication slot 112. Insert holes 140 are formed in the perimeter of the upper body part 110a. By virtue of the insert holes 140, a suture (not shown) can be easily wound around the main body 100 with one end of the suture inserted into and fastened to one of the insert holes 140. It must be understood that the insert holes 140 are not essential elements.

Furthermore, a slit 150 having an approximately "U" shape is formed in the upper surface of the main body 100. The shape of the slit 150 is not limited to that of this embodiment. The slit 150 enables a portion enclosed by the slit 150 to be bent backward when a user clamps a suture needle using pincers or the like, thus making it easy for the user to reliably and easily clamp the suture needle.

The fixing clip 200 is provided on a predetermined portion of the upper surface of the main body 100. The fixing clip 200 has a plurality of insert slots (not designated by a reference numeral) into which the suture needle coupled to a corresponding end of the suture wound around the main body 100 in the winding depression 120 is inserted and fixed. Preferably, the fixing clip 200 is provided on the upper surface of the main body 100 at a position adjacent to the slit 150.

The protrusion rods 300 are provided in the winding depression 120 formed in the main body 100, that is, on an inner sidewall of the winding depression 120. Particularly, the protrusion rods 300 are provided on a curved portion of the inner sidewall of the winding depression 120 and support the suture so that the suture can be prevented from making direct contact with the inner sidewall of at least the curved portion of the winding depression 120, thus reducing friction between the suture and the sidewall. Preferably, at least two protrusion rods 300 are provided on the curved surface of the sidewall of the winding depression 120 at positions spaced apart from each other at regular intervals. Most preferably, four protrusion rods 300 are provided. Of course, the number of protrusion rods 300 is not limited to the above-stated examples. However, if the number of protrusion rods 300 is comparatively large, the friction between the protrusion rods 300 and the suture may be excessively increased. Furthermore, it is obvious that the protrusion rods 300 may be provided on the entirety of the winding depression 120 at regular intervals as well as on the curved surface of the sidewall of the winding depression 120. In addition, although each protrusion rod 300 has been illustrated in the drawings as having a cylindrical shape, it is not limited to this example. For instance, each protrusion rod 300 may have a polygonal rod shape, e.g., a triangular or rectangular rod shape.

Hereinbelow, the operation and usage of the medical suture package according to the first embodiment of the present invention having the above-mentioned construction will be described.

Figure 4A:
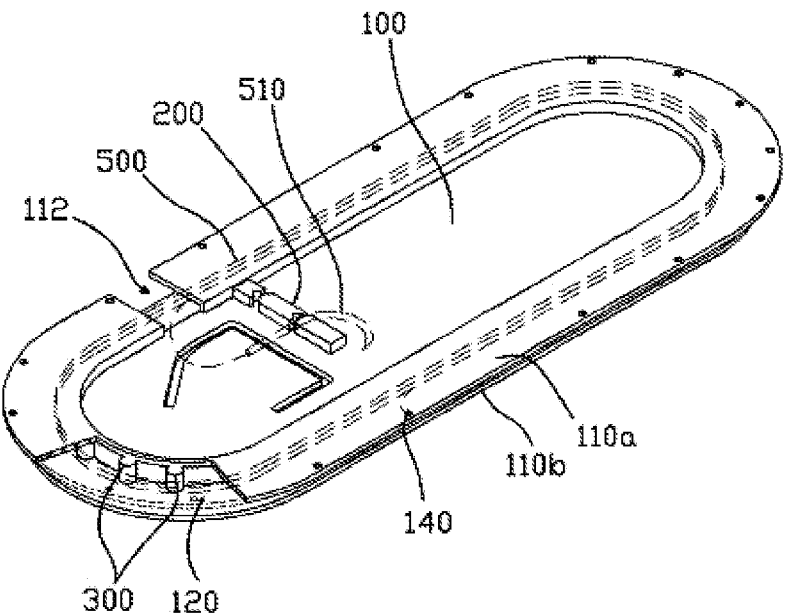
FIG. 4A is a schematic perspective view showing a suture wound around the medical suture package according to the first embodiment of the present invention.
Figure 4B:
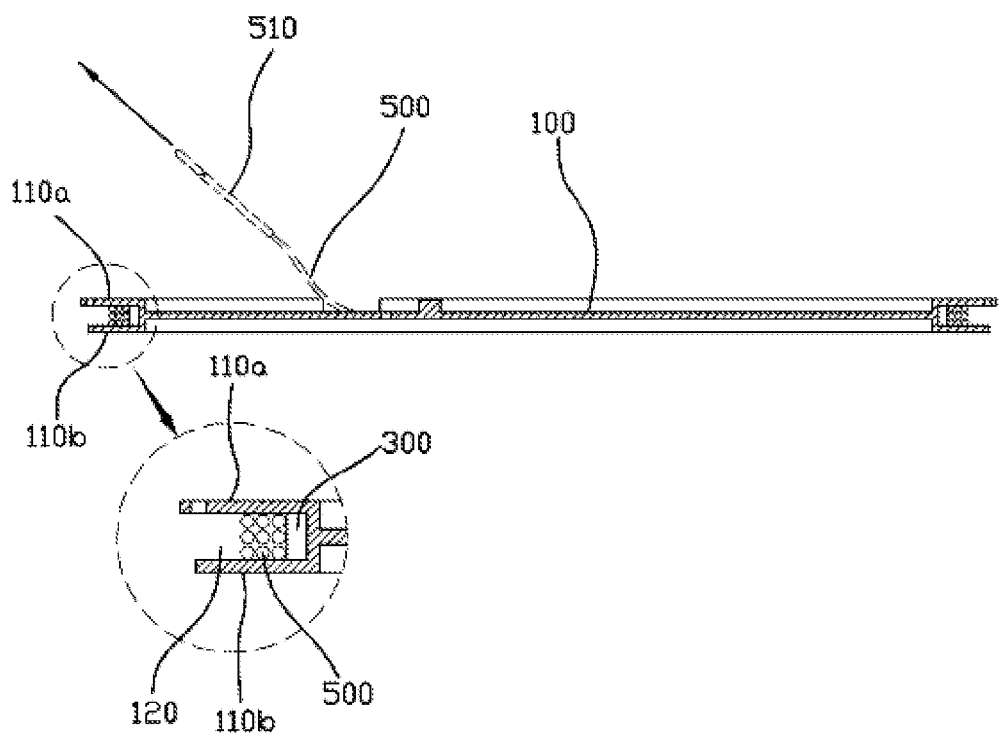
FIG. 4B is a schematic side sectional view illustrating a process of drawing the suture out of the medical suture package according to the first embodiment of the present invention.

FIG. 4A is a schematic perspective view showing the suture wound around the medical suture package according to the first embodiment of the present invention. FIG. 4B is a schematic side sectional view illustrating a process of drawing the suture out of the medical suture package according to the first embodiment of the present invention.

Referring to FIG. 4A, the suture 500 is wound around the main body 100 in the winding depression 120. Winding methods are classified into two kinds of methods.

In one method, the suture needle 510 provided on one end of the suture 500 is fixed to the fixing clip 200 provided on the upper surface of the main body 100, and then the suture is wound around the main body 100. In the other method, the suture 500 is first wound around the main body 100, and then the suture needle 510 provided on the corresponding end of the suture 500 is fixed to the fixing clip 200.

According to the former method, the suture needle 510 is first fixed to the fixing clip 200 provided on the upper surface of the main body 100. The suture 500 is thereafter drawn into the winding depression 120 through the communication slot 112 formed at the predetermined position in the upper body part 110a of the main body 100. Subsequently, the suture 500 is wound around the main body 100 along the winding depression 120. Thereafter, the end of the suture 500 is fitted into an adjacent one of the insert holes 140 formed in the upper body part 110a to prevent the suture 500 from being loosened from the main body 100, thus completing the suture winding operation.

According to the latter method, the suture 500 is first wound around the main body 100 in the winding depression 120 and then drawn onto the upper surface of the main body 100 through the communication slot 112 formed in the upper body part 110a. Subsequently, the suture needle 510 provided on the corresponding end of the end of the suture 500 is fixed to the fixing clip 200, thus completing the suture winding operation. In this case, there is no need for inserting the other end of the suture 500 into one of the insert holes 140 formed in the upper body part 110a because the other end of the suture 500 is disposed at the innermost position of the suture 500 wound around the main body 100.

As such, after the operation of winding the suture 500 around the medical suture package of the present invention has been completed, it is sterilized and packed in a separate package bag before being marketed.

For the use of the medical suture package of the first embodiment, a medical worker opens the package bag, uses medical pincers (not shown) to clamp the suture needle 510 that is held by the fixing clip 200 as shown in FIG. 4B, and then pulls the suture needle 510 in a diagonal direction. Here, because the slit 150 is formed in the upper surface of the main body 100, the portion enclosed by the slit 150 can be pushed downward when the pincers are used to clamp the suture needle, thus making the operation of clamping the suture needle easy. The suture 500 that has been wound around the main body 100 in the winding depression 120 can be drawn out of the winding depression 120 by force of pulling the suture 500. Although one end of the suture 500 is fitted in any one of the insert holes 140 formed in the upper body part 110a, the suture 500 can be easily drawn out of the winding depression 120 because the end of the suture 500 is not forcibly fixed to the insert hole 140.

During the operation of drawing out the suture 500, the curved surface of the sidewall of the winding depression 120 is highest in frictional force generated between the suture 500 and the sidewall of the winding depression 120. Given this, the protrusion rods 300 are provided on the curved surface so as to support the suture 500 and reduce the frictional surface, thus minimizing the friction, thereby making it easy to draw out the suture 500. Furthermore, the medical suture package of the present invention is manufactured into a single body without having a separate cover, unlike the conventional technique. Therefore, the present invention does not cause a problem of the suture 500 being caught in space between two parts during the process of drawing out the suture 500, thus preventing a curling phenomenon, which may be caused during the suture drawing-out process.

Hereinbelow, a second embodiment of the present invention will be described in detail. In the following description of the second embodiment, the same reference numerals are used to designate the same or similar components as those of the first embodiment, and the detailed description thereof will be omitted.

Figure 5:
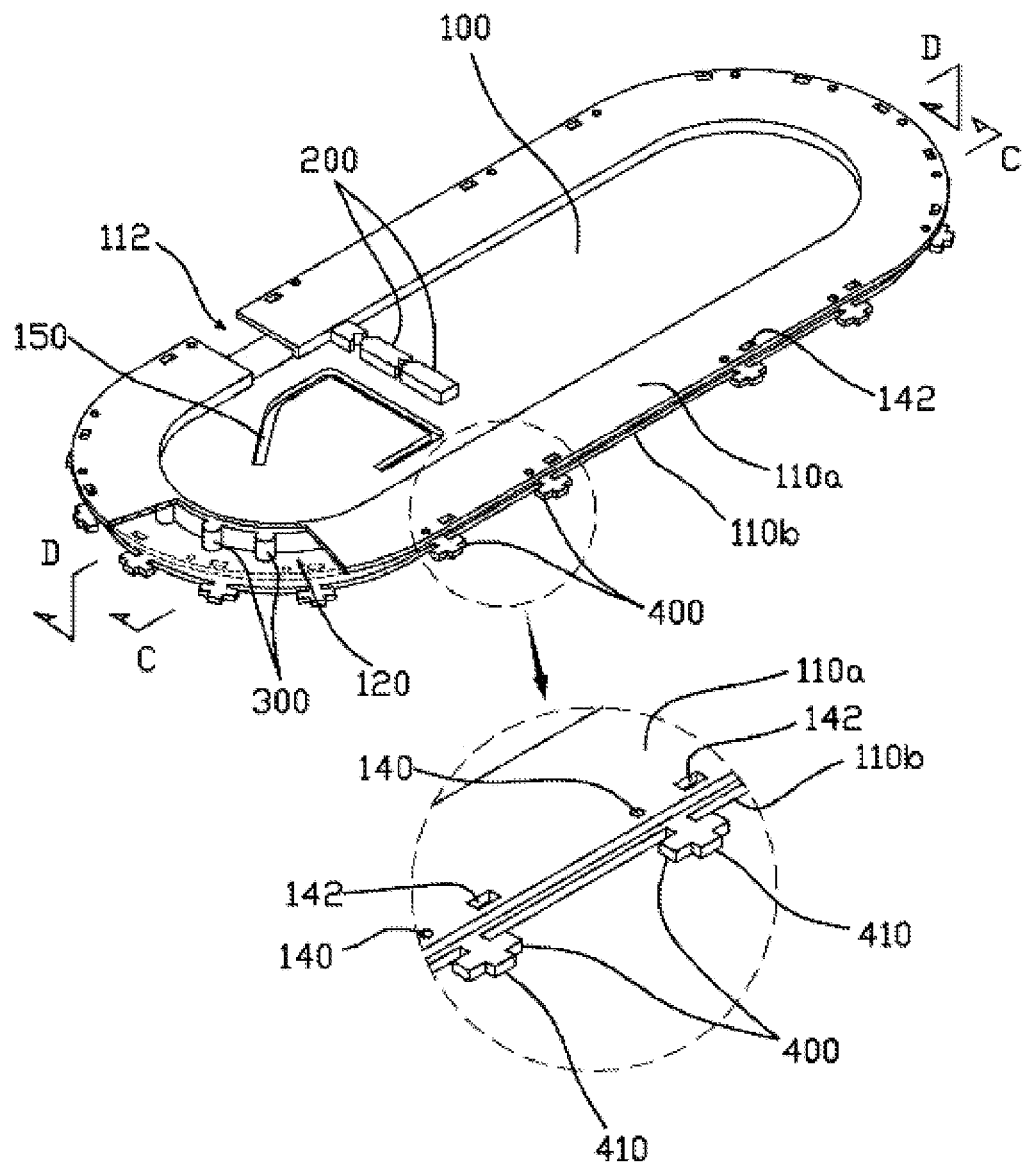
FIG. 5 is a partially-exploded perspective view illustrating a medical suture package according to a second embodiment of the present invention.
Figure 6:
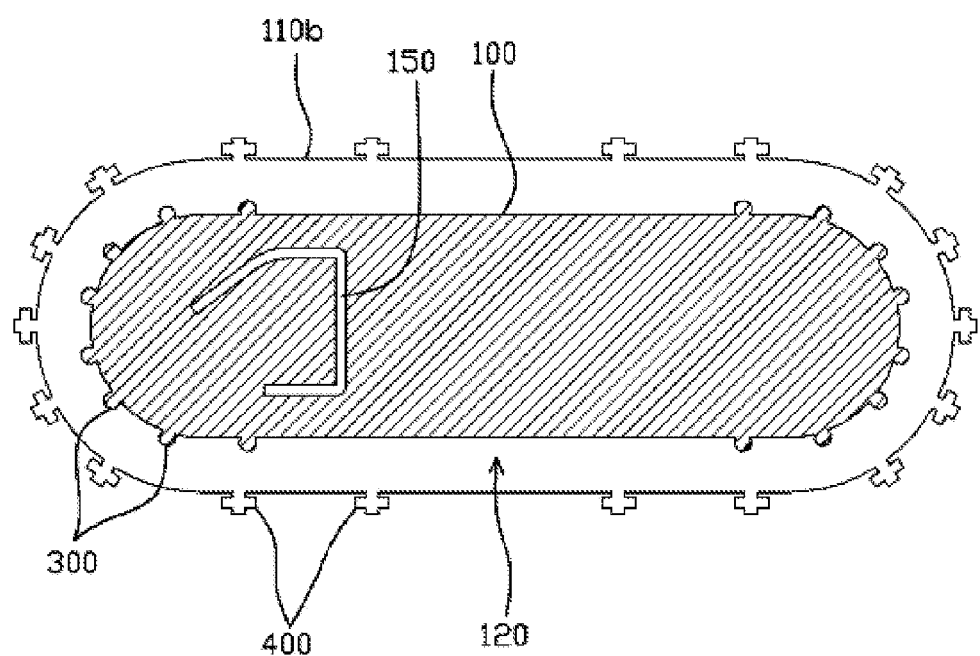
FIG. 6 is a sectional view taken along line C-C of FIG. 5.
Figure 7:
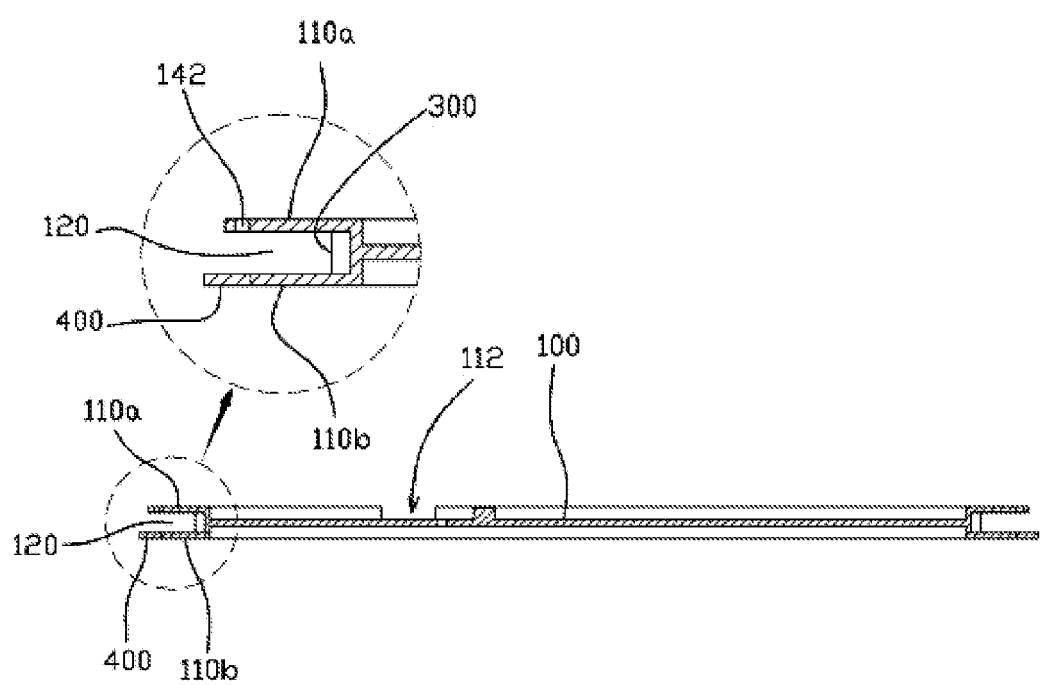
FIG. 7 is a sectional view taken along line D-D of FIG. 5.

FIG. 5 is a partially-exploded perspective view illustrating a medical suture package according to the second embodiment of the present invention. FIG. 6 is a sectional view taken along line C-C of FIG. 5. FIG. 7 is a sectional view taken along line D-D of FIG. 5.

Referring to FIGS. 5 through 7, the medical suture package according to the second embodiment of the present invention includes a main body 100, a fixing clip 200, protrusion rods 300, and supports 400.

The main body 100 has an elliptical shape and includes upper and lower body parts 110a and 110b that are respectively provided at upper and lower positions along the perimeter of the main body 100, with a winding depression 120 formed between the upper and lower body parts 110a and 110b such that it is open outward. A communication slot 112 is formed at a predetermined position in the upper body part 110a. A plurality of insert holes 140 are also formed in the upper body part 110a. The main body 100 according to the second embodiment is the same as that of the first embodiment described above; therefore, detailed explanation thereof will be omitted. However, unlike the first embodiment, in the second embodiment, a plurality of coupling holes 142 are formed in the upper body part 110a of the main body 100 at predetermined positions adjacent to the respective insert holes 140 formed in the perimeter of the upper body part 110a.

The fixing clip 200 and the protrusion rods 300 are also the same as those of the first embodiment, and further description thereof is deemed unnecessary.

In the second embodiment, the supports 400 are provided between the upper and lower body parts 110a and 110b of the main body 100 along the perimeter of the main body 100. The supports 400 support the upper and lower parts 110a and 110b so that even if external force is applied to the main body 100, the upper and lower parts 110a and 110b can be prevented from making close contact with each other, whereby the shape of the winding depression 120 defined between the upper and lower body parts 110a and 110b can be maintained. An insert part 410 protrudes from an outer end of each support 400. The insert parts 410 of the supports 400 are inserted into the respective coupling holes 142 formed in the upper body part 110a, thus supporting the upper and lower body parts 110a and 110b. Furthermore, each support 400 is preferably configured such that an inner end thereof is coupled to the peripheral edge of the lower body part 110b, thus eliminating the likelihood of loss of the support 400, and enhancing the efficiency of manufacturing work. When the support 400 is bent upward on the inner end thereof coupled to the lower body part 110b, the support 400 is disposed between the upper and lower body parts 110a and 110b and coupled to the upper body part 110a by the insert part 410 fitted into the corresponding coupling hole 142.

Alternatively, the supports 400 may be configured such that the inner ends thereof are coupled to the upper body part 110a and the outer ends thereof are fitted into the respective coupling holes 142 formed in the lower body part 110b. The purpose and effect of this configuration are the same as those of the above-mentioned configuration of the second embodiment.

Hereinbelow, the operation and usage of the medical suture package according to the second embodiment of the present invention having the above-mentioned construction will be described.

Figure 8A:
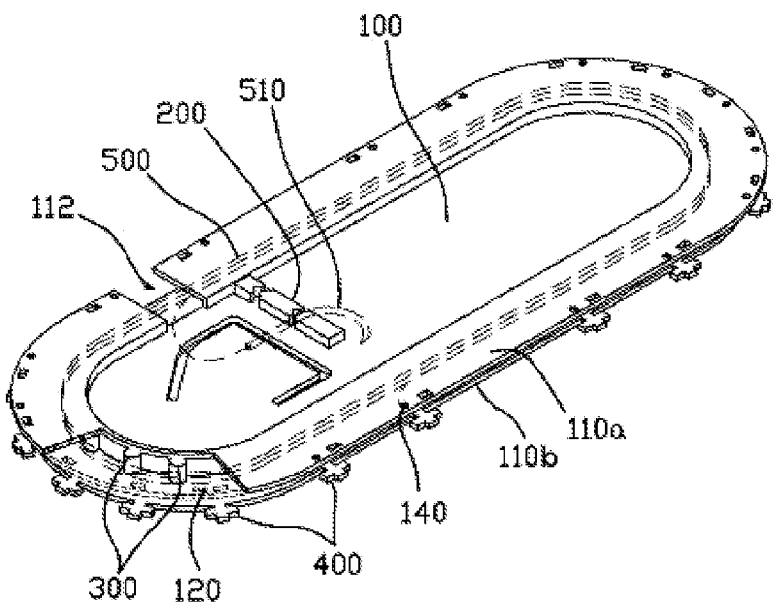
FIGS. 8A and 8B are respectively a schematic perspective view and a schematic side sectional view showing a suture wound around the medical suture package according to the second embodiment of the present invention.
Figure 8B:
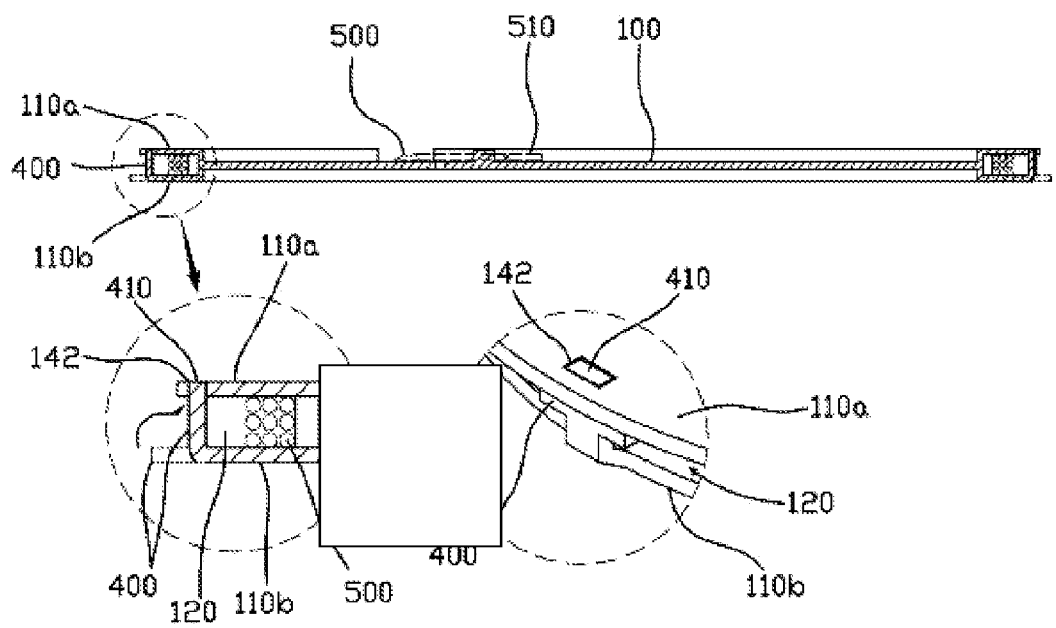
Figure 9:
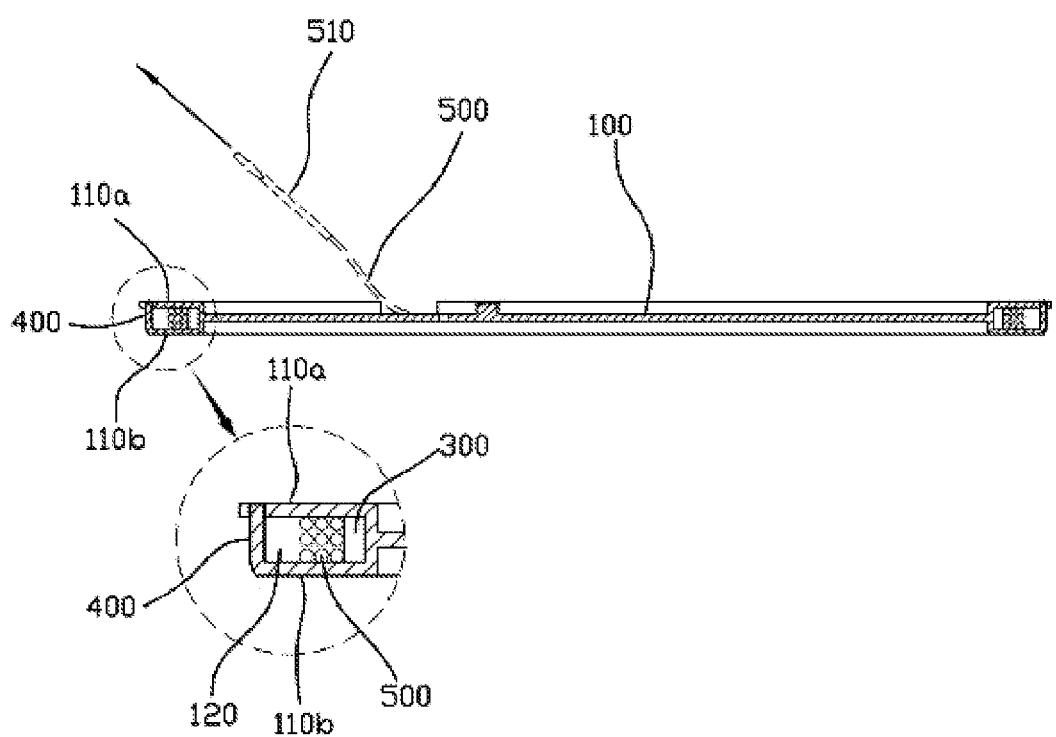
FIG. 9 is a schematic side sectional view illustrating a process of drawing the suture out of the medical suture package according to the second embodiment of the present invention.

FIGS. 8A and 8B are respectively a schematic perspective view and a schematic side sectional view showing a suture wound around the medical suture package according to the second embodiment of the present invention. FIG. 9 is a schematic side sectional view illustrating a process of drawing the suture out of the medical suture package according to the second embodiment of the present invention.

Referring to FIG. 8A, the method of winding the suture 500 around the medical suture package according to the second embodiment is also the same as that of the first embodiment; therefore, further explanation thereof will be omitted. However, in the second embodiment, the suture 500 is wound the main body 100 with the winding depression 120 opened by horizontally orienting the supports 400 coupled to the lower body part 110b of the main body 100.

As shown in FIG. 8B, after the operation of winding the suture 500 around the main body 100 in the winding depression 120 has been completed, the supports 400 provided on the peripheral edge of the lower body part 110b are bent upward such that the supports 400 are disposed between the upper and lower body parts 110a and 110b, and then the insert parts 410 provided on the outer ends of the supports 400 are fitted into the respective coupling holes 142 of the upper body part 110a. In this embodiment, the supports 400 partially cover the winding depression 120 and thus function to protect the wound suture 500. In addition, even if external force that clamps the upper and lower body parts 110a and 110b is applied thereto, the supports 400 can prevent the upper and lower body parts 110a and 110b from making close contact with each other, thereby preventing the winding depression 120 in which the suture 500 is wound around the main body 100 from being deformed.

If the width of the winding depression 120 is reduced by external force, portions of the wound suture 500 become close to each other, thus making the operation of drawing out the suture 500 difficult.

For the use of the medical suture package of the second embodiment, a medical worker uses medical pincers (not shown) to clamp the suture needle 510 that is held by the fixing clip 200 as shown in FIG. 9, and then pulls the suture needle 510 in a diagonal direction. During this suture drawing-out process, the protrusion rods 300 can reduce friction between the suture 500 and the main body 100, thus facilitating the suture drawing-out operation. Even if excessive external force is applied to the main body 100 when the medical worker holds the main body 100, the upper and lower body parts 110a and 110b can be prevented from making contact with each other because the supports 440 are provided between the upper and lower body parts 110a and 110b. Thereby, the shape of the winding depression 120 can be reliably maintained. Consequently, the operation of drawing out the suture 500 can be more easily conducted, thus enhancing convenience in use.

Figure 10:
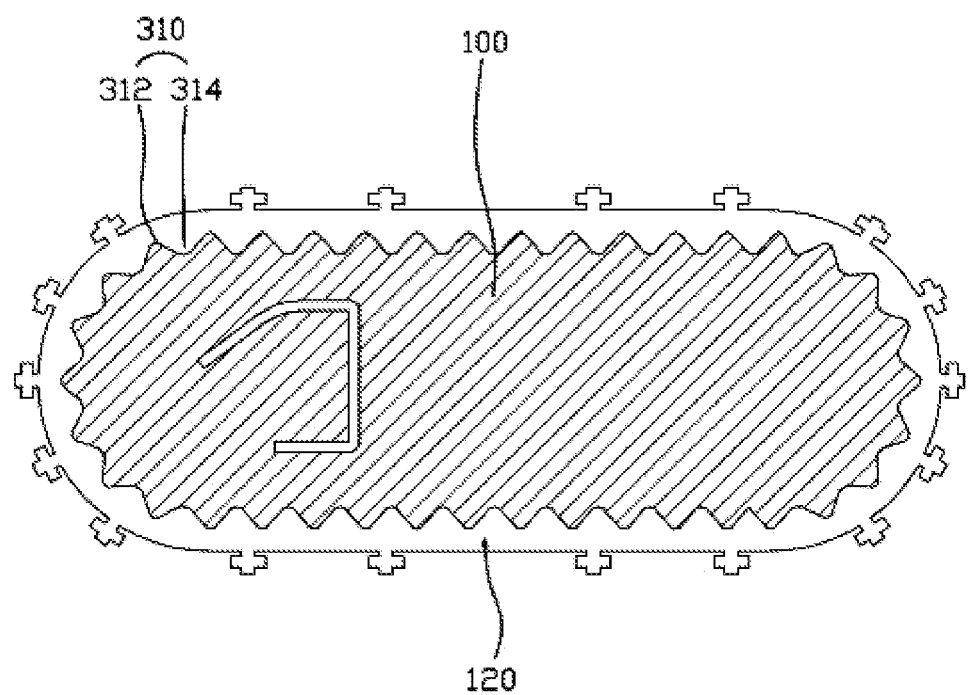
FIG. 10 is a plan sectional view illustrating a main body of a medical suture package according to a third embodiment of the present invention.

FIG. 10 is a plan sectional view illustrating a main body of a medical suture package according to a third embodiment of the present invention.

Referring to the drawing, in lieu of the above-mentioned protrusion rods 300, a saw-toothed part 310 may be provided on the sidewall of the winding depression 120 formed in the main body 100. The saw-toothed part 310 includes protrusions 312 and recesses 314 that are alternately provided. The saw-toothed part 310 can provide the effect of reducing friction between the suture and the main body in the same manner as that of the protrusion rods 30.

As described above, a medical suture package according to the present invention has an improved structure such that when a suture is drawn out of the package, the friction between the suture and the package can be reduced, thus preventing a curling phenomenon, and making it easy to draw out the suture. Particularly, supports may be provided between upper and lower body parts that define therebetween a winding depression in which the suture is wound around the main body. In this case, even if external force is applied to the main body, the winding depression in which the suture is wound around the main body can be maintained in its original shape by the supports, thus ensuring the operation of drawing out the suture, thereby markedly enhancing convenience in use.

The above descriptions are supposed to describe the features and technical advantages in wider ranges in an attempt to help better understand the accompanying claims. Additional features and advantages belonging to the claims have been described in the above. It is obvious that an ordinary person with skills can easily perform the purposes similar with those of the present invention in terms of the concepts and feature embodiments of the present invention.

In addition, in order to perform the same purposes of the present invention, all changes and modifications that fall within the meets and bounds of the claims, or equivalences of such meets and bounds are therefore intended to be embraced by the appended claims without departing from the inherent technical concepts and spirits of the present invention.

What is claimed is:

1. A medical suture package, comprising:
   a main body including upper and lower body parts respectively provided at upper and lower positions along a perimeter of the main body, with a winding depression formed between the upper and lower body parts such that the winding depression is open outward so that a suture is wound around the main body in the winding depression, and with a plurality of coupling holes formed in a perimeter of the upper body part;
   a fixing clip provided at a predetermined position on an upper surface of the main body so that a suture needle provided on a first end of the suture wound around the main body in the winding depression is fitted into and held by the fixing clip;
   a protrusion rod provided on a curved surface of an inner sidewall of the winding depression formed in the main body, the protrusion rod supporting the suture so that the suture wound around the main body is prevented from making direct contact with at least the curved surface of the inner sidewall of the winding depression; and
   a plurality of supports disposed between the upper and lower body parts of the main body, the supports supporting the upper and lower body parts so that even when an external force is applied to the main body, the upper and lower body parts are prevented from making contact with each other and the winding depression is thus maintained in shape, with an insert part provided on a first end of each of the supports, and each insert part being fitted into the corresponding coupling hole of the upper body part,
   wherein a second end of each of the support is coupled to the lower body part so that, when the support is bent upward on the second end thereof, the support is disposed between the upper and lower body parts and coupled to the upper body part by the insert part fitted into the corresponding coupling hole.

2. The medical suture package as set forth in claim 1, wherein a communication slot is formed at a predetermined position in the upper body part so that the winding depression communicates with the fixing clip through the communication slot.

3. The medical suture package as set forth in claim 1, wherein a plurality of insert holes are formed in at least either of the upper and lower body parts so that a second end of the suture can be fitted into any one of the insert holes.

4. A medical suture package, comprising:
   a main body;
   an upper body part provided at an upper positon along a perimeter of the main body and including a plurality of coupling holes; and
   a lower body part positioned at a lower position along the perimeter of the main body forming a winding depression between the upper and lower body parts such that the winding depression is open outward and configured to receive a suture wound around the main body in the winding depression,
   wherein the lower body comprises a plurality of supports configured to be bent upward and support the upper body part at a predetermined distance from the lower body part, and
   wherein each of the plurality of supports includes an insert part configured to insert upwardly into a corresponding coupling hole in the upper body part.

5. The medical suture package of claim 4, further comprising:
   a fixing clip provided at a predetermined position on an upper surface of the main body and configured to fix a suture needle.

6. The medical suture package of claim 4, further comprising:
   a protrusion rod provided on a curved surface of an inner sidewall of the winding depression, the protrusion rod configured to support the suture so that the suture wound around the inner sidewall is prevented from making direct contact with at least a portion of the curved surface of the inner sidewall of the winding depression.

7. The medical suture package of claim 5, further comprising
   a communication slot formed at a predetermined position in the upper body part so that the winding depression communicates with the fixing clip through the communication slot.

8. The medical suture package of claim 4, further comprising:
   an insert hole formed in at least one of the upper or lower body parts so that an end of the suture can be fitted into the insert hole.

9. The medical suture package of claim 4, further comprising:
   a saw-toothed part provided on an inner sidewall of the winding depression for reducing a contact surface area between the suture and the inner sidewall and minimizing friction therebetween, the saw-toothed part comprising protrusions and recesses that alternate with each other.

* * * * *